United States Patent [19]
Hayashi et al.

[11] B 4,001,309
[45] Jan. 4, 1977

[54] METHOD OF PREPARING POLYFLUOROALKYL GROUP CONTAINING COMPOUNDS
[75] Inventors: Takao Hayashi; Masashi Matsuo, both of Yokohama, Japan
[73] Assignee: Asahi Glass Company, Ltd., Tokyo, Japan
[22] Filed: Apr. 16, 1973
[21] Appl. No.: 351,455
[44] Published under the second Trial Voluntary Protest Program on February 24, 1976 as document No. B 351,455.
[52] U.S. Cl. .............................. 260/493; 260/486 H; 260/499; 260/638 R; 260/643 D; 260/963
[51] Int. Cl.[2] ................. C07C 27/00; C07C 29/00; C07C 67/20
[58] Field of Search ...................... 260/493, 638 R
[56] References Cited
UNITED STATES PATENTS 3,157,705 11/1964 Pearce ........................... 260/631 R
3,226,449 12/1965 Blanchard et al. ................ 260/493
3,562,315 2/1971 Cookson et al. ................. 260/493

*Primary Examiner*—Vivian Garner
*Attorney, Agent, or Firm*—Oblon, Fisher, Spivak, McClelland & Maier

[57] ABSTRACT

Polyfluoroalkyl group-containing compounds are prepared according to the following reaction:

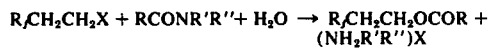

$$R_fCH_2CH_2X + RCONR'R'' + H_2O \rightarrow R_fCH_2CH_2OCOR + (NH_2R'R'')X$$

wherein $R_f$ represents perfluoroalkyl groups containing $C_{1-23}$ carbon atoms, R, R' and R'' represent hydrogen atoms or lower alkyl groups, and X represents bromine atoms or iodine atoms. The polyfluoroalkyl group-containing esters having the formula $R_fCH_2CH_2OCOR$, are converted by hydrolysis to polyfluoroalkyl group-containing alcohols having the formula $R_fCH_2CH_2OH$ wherein $R_f$ is defined as above.

12 Claims, No Drawings

METHOD OF PREPARING POLYFLUOROALKYL GROUP CONTAINING COMPOUNDS

BACKGROUND OF THE INVENTION

1. Field of the Invention

This invention relates to a method for preparing polyfluoroalkyl group containing compounds. More particularly, it relates to a method for preparing polyfluoroalkyl group containing esters, or alcohols or mixtures thereof by the following reactions:

$R_fCH_2CH_2X + RCONR'R'' + H_2O \rightarrow R_fCH_2CH_2OCOR + (NH_2R'R'')X$ $R_fCH_2CH_2OCOR + H_2O \rightarrow R_fCH_2CH_2OH + RCOOH$ wherein $R_f$ represents perfluoroalkyl groups containing $C_{1-23}$ carbon atoms, R, R' and R'' represent hydrogen atoms or lower alkyl groups, and X represents bromine atoms or iodine atoms.

2. Description of the Prior Art

The polyfluoroalkyl halides $R_fCH_2CH_2X(X = Br$ or $I)$ are readily available materials. This series of compounds forms a potentially valuable series of intermediates for the synethesis of the corresponding polyfluoroalkyl esters, $R_fCH_2CH_2OCOR$, and polyfluoroalkyl alcohols, $R_fCH_2CH_2OH$, which are useful products, if suitable means could be provided for converting the polyfluoroalkyl halides to the useful products. These polyfluoroalkyl group containing esters and alcohols are, in turn, useful intermediates for the preparation of various useful products such as water and oil repellents, surface active agents, lubricants, and the like.

A method is known for the conversion of these halides to the corresponding esters which involves the reaction of a polyfluoroalkyl halide with silver acetate. The resulting esters are then converted to the corresponding alcohols by hydrolysis. Although the yields are usually not too low, the reaction is slow and the expense of reconverting the silver halide produced to a useful form of silver makes the process uneconomical. Naturally, silver is very expensive so it is necessary to recover it and to reuse it.

U.S. Pat. No. 3,171,861 discloses various processes for the preparation of perfluoroalkyl group containing alcohols. This process has the disadvantages of many reaction steps, severe reaction conditions, low yields of products, and the like. U.S. Pat. No. 3,239,557 discloses another method for converting polyfluoroalkyl halides to the corresponding esters by reacting the halides with alkali metal carboxylates in anhydrous monohydric alcoholic solvents. In this method, olefin by-products having the formula $R_fCH=CH_2$ are readily formed by dehydrohalogenation of the polyfluoroalkyl halide. Moreover, when the polyfluoroalkyl halides are reacted with an alkali metal hydroxide, the desired polyfluoroalkyl alcohols, $R_fCH_2CH_2OH$, are not obtained because only olefins $R_fCH=CH_2$ are obtained.

A need, therefore, exists for a method of converting polyfluoroalkyl halides to the corresponding alcohols and esters in high yields without using expensive reagents and without producing appreciable amounts of undesirable by-products.

SUMMARY OF THE INVENTION

Accordingly, one object of this invention is to provide a novel method of converting halides having the formula $R_fCH_2CH_2X$ to the corresponding esters having the formula $R_fCH_2CH_2OCOR$ and/or the corresponding alcohols having the formula $R_fCH_2CH_2OH$, wherein X is Br or I.

Another object is to provide a method which gives the esters and/or the alcohols in significantly high yields.

Still another object is to provide a method which uses relatively inexpensive reagents for the conversion of the polyfluoroalkyl halides which reduces the dehydrohalogenation of the halides to olefinic products.

Yet another object is to provide significantly useful polyfluoroalkyl esters and/or polyfluoroalkyl alcohols.

Briefly, these and other objects of this invention as hereinafter will become readily apparent can be attained by a method for preparing polyfluoroalkyl group containing compounds having the formula $R_fCH_2CH_2Z$ wherein $R_f$ represents a perfluoroalkyl group containing $C_{1-23}$ carbon atoms, Z represents —OH or —OCOR and R represents a hydrogen atom or a lower alkyl group which comprises reacting a polyfluoroalkyl halide having the formula $R_fCH_2CH_X$, wherein $R_f$ is defined as before and X is Br or I, with an amide having the formula RCONR'R'', wherein R, R' and R'' represent hydrogen atoms or lower alkyl groups, and water. The synthesis of the polyfluoroalkyl esters and alcohols is shown by the following equations.

$R_fCH_2CH_2X + RCONR'R'' + H_2O \rightarrow R_fCH_2CH_2OCOR + [R'R''NH_2]X$ $R_fCH_2CH_2OCOR + H_2O \rightarrow R_fCH_2CH_2OH + RCO_2H$ In accordance with the process of this invention, the conversion of the starting polyfluoroalkyl halides can be in the range of 90–100% and the formation of by-product olefin, $R_fCH=CH_2$, can be substantially reduced. Thus, the desired polyfluoroalkyl group containing esters $R_fCH_2CH_2OCOR$ and the corresponding alcohols $R_fCH_2CH_2OH$ can be obtained in high yields. In the reaction according to this invention, a 1 : 1 : 1 mole ratio of polyfluoroalkyl halide : water : amide produces the desired ester product, while a mole ratio of 1 : 2 : 1 of polyfluoroalkyl halide : water : amide produces the desired alcohol product. Mechanistically it is believed that the polyfluoroalkyl ester is produced from the halide, water and the amide, and that total or partial conversion of the ester to the corresponding alcohol by hydrolysis is determined by the amount of water present in the reaction system. Thus, by controlling the amount of water relative to the polyfluoroalkyl halide, it is possible to obtain an ester as the main product or to obtain the alcohol as the main product or to obtain a mixture of the ester and the alcohol as the main product.

DESCRIPTION OF THE PREFERRED EMBODIMENTS

In this invention, the starting polyfluoroalkyl halides having the formula $R_fCH_2CH_2X$ can be easily obtained by the addition reaction of a perfluoroalkylhalide $(R_fX)$ with ethylene. The addition reaction can be initiated by heating, by a free-radical catalyst, or by irradiation with ultraviolet radiation or ionizing radioactive radiation. These method have been disclosed by Haszeldine et al., in *J. Chem. Soc.* 2856 (1949) and 3041 (1950); by Park et al. in *J. Org. Chem.*, 23, 1166 (1958) and in U.S. Pat. No. 3,145,222.

Suitable polyfluoroalkyl halides having the formula $R_fCH_2CH_2X$ wherein $R_f$ represents perfluoroalkyl groups containing $C_{1-23}$ carbon atoms and X represents bromine or iodine include $CF_3(CF_2)_{0-22}CH_2CH_2I$ com- ,ounds such as $CF_3CH_2CH_2I$, $CF_3(CF_2)_2CH_2CH_2I$, $CF_3(CF_2)_5CH_2CH_2I$, $CF_3(CF_2)_{11}CH_2CH_2I$; $CF_3(CF_2)_{0-20}CH_2CH_2Br$ compounds such as $CF_3CH_2CH_2Br$, $CF_3(CF_2)_2CH_2CH_2Br$, $CF_3(CF_2)_{11}CH_2CH_2Br$; $(CF_3)_2CF(CF_2)_{0-20}CH_2CH_2I$; and $(CF_3)_2CF(CF_2)_{0-20}CH_2CH_2Br$ compounds such as $(CF_3)_2CF(CF_2)_2CH_2CH_2I$, $(CF_3)_2CF(CF_2)_2CH_2CH_2Br$, $(CF_3)_2CF(CF_2)_4CH_2CH_2I$, $(CF_3)_2CF(CF)_4CH_2CH_2Br$, $(CF_3)_2CF(CF_2)_6CH_2CH_2I$, $(CF_3)_2CF(CF_2)_6CH_2CH_2Br$, $(CF_3)_2CF(CF_2)_8CH_2CH_2I$, $(CF_3)_2CF(CF_2)_8CH_2CH_2Br$; and $CF_3(CF_2)_2[CF_2CF(CF_3)]_2CH_2CH_2I$, $CF_3(CF_2)_2[CF_2CF(CF_3)]_2CH_2CH_2Br$, $CF_3(CF_2)_2[CF_2CF(CF_3)]_3CH_2CH_2I$, $CF_3(CF_2)_2[CF_2CF(CF_3)]_3CH_2CH_2Br$, $(CF_3)_2CF[CF_2CF(CF_3)]CH_2CH_2I$, $(CF_3)_2CF[CF_2CF(CF_3)]CH_2CH_2Br$, $(CF_3)_2CF[CF_2CF(CF_3)]_2CH_2CH_2I$, $(CF_3)_2CF[CF_2CF(CF_3)]_2CH_2CH_2Br$, and the like.

Suitable amides having the formula RCONR'R'' wherein R, R' and R'' represent hydrogen atoms or lower alkyl groups include formamide, acetamide, dimethylformamide, diethylformamide, monomethylformamide, monoethylformamide, methylethylformamide, dipropylformamide, dimethylacetamide, and the like.

The term "lower alkyl group" encompasses those alkyl groups containing $C_{1-5}$ carbon atoms, especially $C_{1-3}$ carbon atoms. In this invention it is preferable to use formamide derivatives having the formula HCONR'R'', and especially to use N-lower alkyl mono-substituted formamides or N-lower alkyl di-substituted formamides. In general, the di-substituted formamides are more effective than the mono-substituted formamides. Optimumly, dimethylformamide is used from the viewpoint of availability and its reactivity.

In accordance with the process of this invention, a 100% conversion of the polyfluoroalkyl halide, $R_fCH_2CH_2X$ is possible with a simultaneous reduction in the formation of by-product olefin, $R_fCH = CH_2$, by using N-lower alkyl substituted formamides, HCONR'R'', wherein R' and R'' represent hydrogen atoms or lower alkyl groups as the amide coreactant. By this method the desired polyfluoroalkyl esters and/or alcohols can be produced in selectivities greater than 80%.

In the method of this invention, the mole ratio of water to the polyfluoroalkyl halide is at least 1 : 1 and the mole ratio of the amide to the halide is at least 1 : 1. If the amount of water used is too small, the conversion of the starting polyfluoroalkyl halides is low. If the amount of water used is too great, the selectivity for the desired products is low. Thus, it is preferable that the mole ratio of water to polyfluoroalkyl halide be in the range of 1 : 1 to 10 : 1, especially 1.2 : 1 to 8 : 1. It is also preferable to use an excess of the amide with respect to the halide. Especially, it is preferable to use a large excess of the amide RCONR'R'' by using the amide as a reaction medium. Accordingly, it is preferable to select the mole ratio of the amide to the halide so that it falls within the range of 5 : 1 to 100 : 1, especially 10 : 1 to 40 : 1. Although larger amounts of the amides can be used, there is no advantage in using larger quantities of the amide chiefly because of economic reasons which involve the reactors and recovery of the amide. There is no advantage to be gained by using amounts of amide smaller than the indicated range because the smoothness of the reaction is decreased and the conversion of the halide and the selectivity for the desired compounds are very low.

The amount of polyfluoroalkyl ester, alcohol or mixtures of alcohol and esters desired determines the quantity of water used in the reaction. If the main product desired is the polyfluoroalkyl ester, the stoichiometric mole ratio of water to halide is 1 : 1. If the main product desired is the polyfluoroalkyl alcohol, the stoichiometric mole ratio of water to the halide is 2 : 1. Accordingly, if the ester is the main product desired, the mole ratio of water to the halide is in the range of 1 : 1 to 2 : 1, especially 1.2 : 1 to 1.8 : 1. If the alcohol is the main product desired, then the mole ratio of water to the halide is in the range of 2 : 1 to 10 : 1, preferably 2 : 1 to 8 : 1. Of course, if mixtures of the ester and the alcohol are desired, amounts of water intermediate the two ranges can be used.

In the method of this invention, the amide can be used as the reaction medium as stated above. It is also possible to react the reactants in the presence of a water soluble organic solvent such as dioxane, whereby contact of the reactants increases resulting in a smoother reaction and an increased conversion of the halide.

The reaction of this invention is performed at 80°–200°C, preferably 100°–180°C, especially 120°–160°C. If the reaction temperature is too high, undesirable side reactions increase, whereas if the reaction temperature is too low, the reaction velocity becomes to slow resulting in a decreased yield of product. At the indicated reaction temperatures, the reaction is complete within 1–10 hours. The optimum reaction period is in the range of about 2–6 hours. The reaction pressure is not critical. It is only necessary that the reaction be performed so that close contact of the reagents is maintained. This is suitably accomplished by stirring, agitation, rotation, or shaking.

The resulting ester and/or alcohols can be used after they are separated from the unreacted materials and by-products which include $R_fCH = CH_2$, RCOOH, $(NH_2R'R'')X$ and the like. The mode of separation of the desired products can be accomplished by washing the products with water, fractional distillation, extraction, and the like. For example, if a large amount of water is added to the reaction mixture after the reaction, and the mixture is stirred and then allowed to remain quiescent, the excess amides (RCONR'R''),$(NH_2R'R'')X$, RCOOH, and the like present are transferred to the upper aqueous phase and then separated from the desired products. Any unreacted polyfluoroalkyl halide, by-product olefin, or the like remaining with the product can be removed from the lower phase by distillation procedures and the like.

The polyfluoroalkyl group containing esters and/or alcohols prepared by the process of this invention are useful as intermediates for preparing various useful products. For example, the esters $R_fCH_2CH_2OCOR$ can be converted to unsaturated esters containing perfluoroalkyl groups by transesterification with an alkyl acrylate or an alkyl methacrylate. The unsaturated esters prepared from the product esters can be converted to useful water and oil repellent polymers by a polymerization reaction. Moreover, the esters $R_fCH_2CH_2OCOR$ can be easily converted to the corresponding alcohols $R_fCH_2CH_2OH$ by hydrolysis. The alcohols $R_fCH_2CH_2OH$ can be reacted with organic acids, acid halides or acid anhydrides to obtain useful esters. For example, the alcohols can be converted to unsaturated esters containing perfluoroalkyl groups by esterification with acrylic acid or methacrylic acid, or by transesterification of the unsaturated polyfluoroalkyl esters with alkyl acrylates or alkyl methacrylates.

Phosphate esters containing perfluoroalkyl groups can be obtained by the reaction of the alcohols $R_fCH_2CH_2OH$ with phosphorus oxychloride. These esters are useful as surfactants. Moreover, mixtures of the ester $R_fCH_2CH_2OCOR$ and the alcohol $R_fCH_2CH_2OH$ can be readily converted to perfluoroalkyl group containing unsaturated esters by transesterification with alkyl acrylates or alkyl methacrylates.

In the reaction of this invention, the polyfluoroalkyl group containing alcohols can be directly obtained. However, it is possible to obtain the esters $R_fCH_2CH_2OCOR$ first and then convert the esters to the alcohols by a hydrolysis reaction. The hydrolysis reaction can be easily performed by adding water in quantities from 1–100 times the molar amount of ester present at 80°–160°C with stirring. However, it is preferable to add water in quantities from 5–50 times the molar amount of ester present at 100°–120°C. Of course, any of the common inorganic or organic alkalis, or inorganic or organic acids can be used as catalysts for the hydrolysis reaction. Especially preferable are strong alkaline solutions of sodium hydroxide, potassium hydroxide, and the like.

Having generally described this invention, a further understanding can be obtained by reference to certain specific examples which are provided herein for purposes of illustration only and are not intended to be limiting unless otherwise specified.

EXAMPLES 1–9

Into a 100 ml glass ampoule, 4.74 g of $CF_3(CF_2)_5CH_2CH_2I$ and the quantities of N,N'-dimethylformamide (DMF) and water indicated in Table I below were charged and the mixture was shaken at 150°C for 6 hours. The reaction mixture was washed with 50 ml of water.

The results of gas chromatographic analysis of the weighed oil phase as to the conversion of $C_6F_{13}CH_2CH_2I$ and the selectivity for the products obtained are shown in Table I.

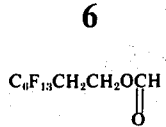

and $C_6F_{13}CH_2CH_2OH$ was 60.4% and 27.3% respectively.

EXAMPLE 11

The procedure of Example 10 was followed except that 6.24 g (10 mmole) of $(CF_3)_2CF(CF_2)_6CH_2CH_2I$, 19.1 g (220 mmole) of N,N'-dimethyl acetamide and 0.27 g (15 mmole) of water were used. The reaction was conducted and the reaction mixture was analyzed. The conversion of $C_9F_{19}CH_2CH_2I$ was 91.1%, and the selectivities for $C_9F_{19}CH_2CH_2OCOCH_3$ and $C_9F_{19}CH_2CH_2OH$ were 57.0% and 15.2% respectively.

EXAMPLE 12

Into a 100 ml glass ampoule, 5.27 g (10 mmole) of $CF_3(CF_2)_7CH_2CH_2Br$, 16.1 g (220 mmole) of N,N'-dimethylformamide, and 0.27 g (15 mmole) of water were charged and the mixture was shaken at 150°C for 8 hours. The reaction mixture was washed with 50 ml of water. The results of gas chromatographic analysis of the weighed oil phase showed a 98.7% conversion of $C_8F_{17}CH_2CH_2I$ while the selectivities for

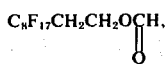

$C_8F_{17}CH_2CH_2OH$ and $C_8F_{17}CH=CH_2$ were 80.1%, 15.3% and 4.6% respectively.

EXAMPLE 13

Into a 100 ml glass ampoule, 5.27 g (10 mmole) of $CF_3(CF_2)_7CH_2CH_2Br$, 16.1 g (220 mmole) of N,N'-dimethylformamide, and 1.08 g (60 mmole) of water were charged and the mixture was shaken at 150°C for 10 hours. The reaction mixture was washed with water and analyzed by gas chromatography. The results

TABLE I

| Example | mole ratio of starting compounds | | | Conversion of $C_6H_{13}C_2H_4I$ | selectivity of product | | |
|---|---|---|---|---|---|---|---|
| | $C_6F_{13}C_2H_4I$ | DMF | $H_2O$ | | $C_6F_{13}C_2H_4OCH$ ‖ O | $C_6F_{13}C_2H_4OH$ | $C_6F_{13}CH=CH_2$ |
| 1 | 1 | 3.1 | 1.5 | 98.3% | 62.8% | 15.7% | 21.5% |
| 2 | 1 | 5.0 | 1.5 | 99.5% | 65.9% | 14.8% | 19.3% |
| 3 | 1 | 10.3 | 1.5 | 99.7% | 71.1% | 16.7% | 12.2% |
| 4 | 1 | 22.0 | 1.5 | 99.7% | 78.5% | 16.1% | 5.4% |
| 5 | 1 | 30.0 | 1.5 | 100.0% | 80.6% | 16.5% | 2.9% |
| 6 | 1 | 22.0 | 1.2 | 94.1% | 91.5% | 4.8% | 3.7% |
| 7 | 1 | 22.0 | 2.0 | 99.2% | 52.8% | 35.2% | 12.0% |
| 8 | 1 | 22.0 | 6.0 | 100.0% | 23.8% | 55.6% | 20.6% |
| 9 | 1 | 22.0 | 8.0 | 100.0% | 3.9% | 73.3% | 22.8% |

EXAMPLE 10

Into a 100 ml glass ampoule, 4.74 g (10 mmole) of $CF_3(CF_2)_5CH_2CH_2I$, 9.9 g (220 mmole) of formamide, 0.27 g (15 mmole) of water and 10.2 g of dioxane were charged, and the mixture was shaken at 150°C for 6 hours. The reaction mixture was then washed with 50 ml of water. The results of a gas chromatographic analysis of the weighted oil phase showed that the conversion of $C_6F_{13}CH_2CH_2I$ was 99.3%, and the selectivities for showed a 99.8% conversion of $C_8F_{17}CH_2CH_2Br$, and the selectivities for

$C_8F_{17}CH_2CH_2OH$ and $C_8F_{17}CH=CH_2$ were 3.2%, 71.5% and 25.3% respectively.

EXAMPLE 14

Into a 50 ml ampoule, 3.92 g (10 mmole) of

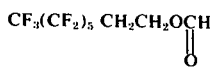

and 4.0 g of a 10 wt. % aqueous KOH solution, were charged and the mixture was shaken at 120°C for 3 hours. The reaction mixture was cooled with water at room temperature, and the water phase was separated. The product was washed with water and the oil phase was weighed and analyzed by gas chromatography. The results showed a 99% conversion of

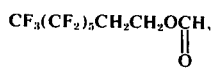

and the selectivity for $CF_3(CF_2)_5CH_2CH_2OH$ was 100%.

Having now fully described the invention, it will be apparent to one of ordinary skill in the art that many changes and modifications can be made thereto without departing from the spirit or scope of the invention as set forth herein.

What is claimed as new and intended to be covered by letters patent is:

1. A method of preparing perfluoroalkyl group containing compounds which comprises reacting a polyfluoroalkyl halide having the formula $R_fCH_2CH_2X$, wherein $R_f$ represents a perfluoroalkyl group containing 1–23 carbon atoms and X represents a bromine atom or an iodine atom, with water and an amide having the formula $RCONR'R''$, wherein R, R' and R'' represent hydrogen atoms or lower alkyl groups under conditions in which the mole ratio of water to said polyfluoroalkyl halide is in the range from 1 : 1 to 10 : 1 and the ratio of said amide to said polyfluoroalkyl halide is at least 1 : 1 at a temperature from about 80° to 200°C.

2. The method of claim 1, wherein the mole ratio of said water to said polyfluoroalkyl halide is 1 : 1 and the mole ratio of said amide to said polyfluoroalkyl halide is 1 : 1.

3. The method of claim 1, wherein the mole ratio of said water to said polyfluoroalkyl halide is in the range from 1 : 1 to 2 : 1 and the ratio of said amide to said polyfluoroalkyl halide is at least 1 : 1.

4. The method of claim 1, wherein the mole ratio of said water to said polyfluoroalkyl halide is in the range from 2 : 1 to 8 : 1 and the ratio of said amide to said polyfluoroalkyl halide is at least 1 : 1.

5. A method of preparing a polyfluoroalkyl group-containing compound having the formula $R_fCH_2CH_2Z$, wherein $R_f$ represents a perfluoroalkyl group containing 1 to 23 carbon atoms, Z is selected from the group consisting of OH, OCOR and mixtures thereof and R represents hydrogen or lower alkyl which comprises reacting 1 mole polyfluoroalkyl halide having the formula $R_fCH_2CH_2X$ wherein $R_f$ is defined as before and X represents a bromine or iodine with 1 to 10 moles of water and 5 to 100 moles of an amide having the formula $RCONR'R''$ wherein R, R' and R'' represent hydrogen or lower alkyl at a temperature from about 80° to 200°C.

6. The method of claim 5, wherein the reaction is conducted at a temperature of from 120° to 160°C.

7. The method of claim 5, wherein R is a hydrogen atom.

8. The method of claim 5, wherein said amide having the formula $RCONR'R''$ is $HCONR'R''$, and at least one of the R' and R'' groups is a lower alkyl group containing 1 to 5 carbon atoms.

9. The method of claim 5, wherein said amide having the formula $RCONR'R''$ is $HCONR'R''$, and both R' and R'' groups are lower alkyl groups containing 1 to 5 carbon atoms.

10. The method of claim 5, wherein said amide having the formula $RCONR'R''$ is dimethylformamide.

11. The method of claim 5, wherein said polyfluoroalkyl halide having the formula $R_fCH_2CH_2X$ is $R_fCH_2CH_2Br$.

12. The method of claim 5, wherein said polyfluoroalkyl halide having the formula $R_fCH_2CH_2X$ is $R_fCH_2CH_2I$.

* * * * *